US00PP29663P2

(12) United States Plant Patent
Barnes

(10) Patent No.: US PP29,663 P2
(45) Date of Patent: Sep. 11, 2018

(54) ***PETUNIA* PLANT NAMED 'BBTUN91601'**

(50) Latin Name: *Petunia X hybrida*
Varietal Denomination: BBTUN91601

(71) Applicant: Brent D. Barnes, Riverside, CA (US)

(72) Inventor: Brent D. Barnes, Riverside, CA (US)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 15/731,454

(22) Filed: Jun. 12, 2017

(51) Int. Cl.
*A01H 5/02* (2018.01)

(52) U.S. Cl.
USPC ..... Plt./356.13
CPC ..... *A01H 5/0277* (2013.01)

(58) Field of Classification Search
USPC ..... Plt./356.13, 356.1
CPC ..... A01H 5/0277
See application file for complete search history.

(56) References Cited

PUBLICATIONS

GTITM UPOVROM Citation for 'BBTUN91601' as per CA PBR 17-9131; Apr. 28, 2017; 1 page.*

* cited by examiner

*Primary Examiner* — Kent L Bell
(74) *Attorney, Agent, or Firm* — C. A. Whealy

(57) ABSTRACT

A new and distinct *Petunia* plant named 'BBTUN91601', characterized by its compact, outwardly spreading and mounding to eventually trailing plant habit; freely branching habit; vigorous growth habit; early and freely flowering habit; white and red purple bi-colored flowers; and good garden performance.

1 Drawing Sheet

Botanical designation: *Petunia* X *hybrida*.
Cultivar denomination: 'BBTUN91601'.

BACKGROUND OF THE INVENTION

The present invention relates to a new and distinct cultivar of *Petunia* plant, botanically known as *Petunia* X *hybrida* and hereinafter referred to by the name 'BBTUN91601'.

The new *Petunia* plant is a product of a planned breeding program conducted by the Inventor in Bonsall, Calif. The objective of the breeding program is to create new freely-branching and uniformly mounding *Petunia* plants with early and freely flowering habit, unique attractive flowers and good garden performance.

The new *Petunia* plant originated from a cross-pollination made by the Inventor on Nov. 23, 2014 in Bonsall, Calif. of a proprietary seedling selection of *Petunia* X *hybrida* identified as code number 14PB201-01, not patented, as the female, or seed, parent with a proprietary seedling selection of *Petunia* X *hybrida* identified as code number 14PB202-01, not patented, as the male, or pollen, parent. The new *Petunia* plant was discovered and selected by the Inventor as a single flowering plant within the progeny of the stated cross-pollination in a controlled greenhouse environment in Bonsall, Calif. on Nov. 2, 2015.

Asexual reproduction of the new *Petunia* plant by vegetative terminal cuttings in a controlled greenhouse environment in Bonsall, Calif. since Nov. 2, 2015 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BBTUN91601'. These characteristics in combination distinguish 'BBTUN91601' as a new and distinct *Petunia* plant:

1. Compact, outwardly spreading and mounding to eventually trailing plant habit.
2. Freely branching habit.
3. Vigorous growth habit.
4. Early and freely flowering habit.
5. White and red purple bi-colored flowers.
6. Good garden performance.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are more freely branching than plants of the female parent selection.
2. Plants of the new *Petunia* and the female parent selection differ in flower color as plants of the female parent selection have pink and light purple bi-colored flowers.

Plants of the new *Petunia* can be compared to plants of the male parent selection. In side-by-side comparisons, plants of the new *Petunia* differ primarily from plants of the male parent selection in the following characteristics:

1. Plants of the new *Petunia* are more freely branching than plants of the male parent selection.

2. Plants of the new *Petunia* and the male parent selection differ in flower color as plants of the male parent selection have magenta and light pink bi-colored flowers.

Plants of the new *Petunia* can be compared to plants of 'Kakegawa S36', disclosed in U.S. Plant Pat. No. 14,037. In side-by-side comparisons, plants of the new *Petunia* differ primarily from plants of 'Kakegawa S36' in the following characteristics:

1. Plants of the new *Petunia* are more mounding than and not as trailing as plants of 'Kakegawa S36'.
2. Plants of the new *Petunia* and 'Kakegawa S36' differ in flower color as plants of 'Kakegawa S36' have solid magenta-colored flowers.
3. Plants of the new *Petunia* are less susceptible to pathogens common to *Petunia* plants than plants of 'Kakegawa S36'.

Plants of the new *Petunia* can also be compared to plants of 'KL 1117', disclosed in U.S. Plant Pat. No. 25,485. In side-by-side comparisons, plants of the new *Petunia* differ primarily from plants of 'KL 1117' in flower color as plants of 'KL 1117' have white-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet is a side perspective view of a typical flowering plant of 'BBTUN91601' grown in a container.

The photograph at the top of the sheet is a close-up view of a typical flowering plant of 'BBTUN91601'.

DETAILED BOTANICAL DESCRIPTION

The aforementioned photographs and following observations and measurements describe plants grown during the early spring in 11.5-cm containers in an acrylic-covered greenhouse in Carleton, Mich. and under cultural practices typical of commercial *Petunia* production. During the production of the plants, day and night temperatures ranged from 18° C. to 27° C. Plants were seven weeks from planting rooted cuttings when the photographs and description were taken. In the following description, color references are made to The Royal Horticultural Society Colour Chart, 2007 Edition, except where general terms of ordinary dictionary significance are used.

Botanical classification: *Petunia* X *hybrida* 'BBTUN91601'.

Parentage:

*Female, or seed, parent*.—Proprietary seedling selection of *Petunia* X *hybrida* identified as code number 14PB201-01, not patented.

*Male, or pollen, parent*.—Proprietary seedling selection of *Petunia* X *hybrida* identified as code number 14PB202-01, not patented.

Propagation:

*Type*.—Terminal vegetative cuttings.

*Time to initiate roots, summer*.—About three to four days at temperatures ranging from 17° C. to 29° C.

*Time to initiate roots, winter*.—About five to seven days at temperatures ranging from 17° C. to 21° C.

*Time to produce a rooted plant, summer*.—About three weeks at temperatures ranging from 17° C. to 29° C.

*Time to produce a rooted plant, winter*.—About four weeks at temperatures ranging from 17° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact, outwardly spreading and mounding to eventually trailing plant habit; freely branching habit with about eight primary lateral branches with three to four secondary lateral branches per primary lateral branch developing; dense and bushy appearance; pinching enhances development of lateral branches; vigorous growth habit.

*Plant height, soil level to top of foliar plane*.—About 10 cm.

*Plant height, soil level to top of floral plane*.—About 13 cm.

*Plant diameter* (*area of spread*).—About 35 cm.

*Lateral branches*.—Length: About 19 cm. Diameter: About 2.5 mm. Internode length: About 1.5 cm. Strength: Strong. Aspect: Initially upright then outwardly spreading. Texture and luster: Pubescent; matte. Color, developing: Close to 146C. Color, developed: Close to 146B.

Leaf description:

*Arrangement*.—Alternate before flowering; opposite after flowers develop; leaves simple.

*Length*.—About 3.2 cm.

*Width*.—About 2.4 cm.

*Shape*.—Elliptical, rounded.

*Apex*.—Broadly acute.

*Base*.—Attenuate.

*Margin*.—Entire.

*Texture and luster, upper and lower surfaces*.—Minute pubescence; matte.

*Venation pattern*.—Pinnate, arcuate.

*Color*.—Developing leaves, upper and lower surfaces: Close to 146A. Fully expanded leaves, upper surface: Close to N137A; venation, close to 147B. Fully expanded leaves, lower surface: Close to 147B; venation, close to 147B.

*Petioles*.—Length: About 7 mm. Diameter: About 3 mm. Strength: Moderately strong. Texture and luster, upper and lower surfaces: Minute pubescence; matte. Color, upper surface: Close to 146B. Color, lower surface: Close to 146C.

Flower description:

*Flower type and flowering habit*.—Single axillary salverform flowers; flowers face mostly upward to outwardly; freely flowering habit with about more than 155 flowers developing per plant during the flowering season.

*Natural flowering season*.—Long day responsive; long flowering period, plants flower from early spring until frost in the autumn, flowering continuous during this period; early flowering habit, plants begin flowering about six weeks after planting.

*Flower longevity on the plant*.—About four to five days; flowers persistent.

*Fragrance*.—None detected.

*Flower buds*.—Length: About 3.3 cm. Diameter: About 7 mm. Shape: Oblong, elongate. Texture and luster: Pubescent; matte. Color: Close to 157A to 157B.

*Flower diameter*.—About 4 cm by 4.4 cm.

*Flower depth* (*height*).—About 4 cm.

*Throat diameter, distal*.—About 1.1 cm.

*Tube length*.—About 3 cm.

*Tube diameter*.—About 8 mm.

*Petals*.—Quantity and arrangement: Five petals fused in a single salverform whorl. Petal lobe length (from throat): About 1.9 cm. Petal lobe width: About 2.2 cm. Petal lobe shape: Fan-shaped. Petal lobe apex: Broadly acute. Petal lobe margin: Entire, undulate. Petal lobe texture and luster, upper surface: Smooth, glabrous; velvety; matte. Petal lobe texture and luster, lower surface: Sparsely pubescent; matte. Throat texture: Smooth, glabrous. Tube texture: Pubescent. Color: When opening, upper surface: Close to NN155D and 77A. When opening, lower surface: Close to 157D and N77C. Fully opened, upper surface: Close to NN155D and brighter than 72A; venation, close to 71A; color does not change with development. Fully opened, lower surface: Close to NN155D and 77B; venation, close to N79B; color does not change with development. Flower throat (inside): Close to N82D; venation, close to 79C. Flower tube (outside): Close to N77D; venation, close to 197B.

*Sepals*.—Quantity and arrangement: Five sepals fused in a single star-shaped whorl. Calyx length: About 1.6 cm. Calyx diameter: About 1.8 cm. Length: About 1.5 cm. Width: About 3 mm. Shape: Ligulate. Apex: Rounded. Margin: Entire. Texture and luster, upper and lower surfaces: Minute pubescence; matte. Color: When opening, upper and lower surfaces: Close to 146A. Fully developed, upper surface: Close to N137A. Fully developed, lower surface: Close to N137B.

*Peduncles*.—Length: About 1.7 cm. Width: About 1.5 mm. Strength: Strong. Angle: About 45° to 55° from the stem axis. Texture and luster: Pubescent; matte. Color: Close to 146B.

*Reproductive organs*.—Stamens: Quantity per flower: Five. Filament length: About 1.5 cm. Filament color: Close to 145D. Anther length: About 1.5 mm. Anther shape: Round. Anther color: Close to 92C. Pollen amount: Moderate. Pollen color: Close to 91A. Pistils: Quantity per flower: One. Pistil length: About 2.3 cm. Style length: About 1.7 cm. Style color: Close to 145C. Stigma diameter: About 2 mm. Stigma shape: Round. Stigma color: Close to 146A. Ovary color: Close to 145B.

*Seeds and fruits*.—Seed and fruit development has not been observed on plants of the new *Petunia* to date.

Pathogen & pest resistance: Plants of the new *Petunia* have not been noted to be resistant to pathogens or pests common to *Petunia* plants.

Garden performance: Plants of the new *Petunia* have been observed to have good garden performance and have been observed to tolerate rain, wind and temperatures ranging from about 1° C. to about 40° C.

It is claimed:

1. A new and distinct *Petunia* plant named 'BBTUN91601' as illustrated and described.

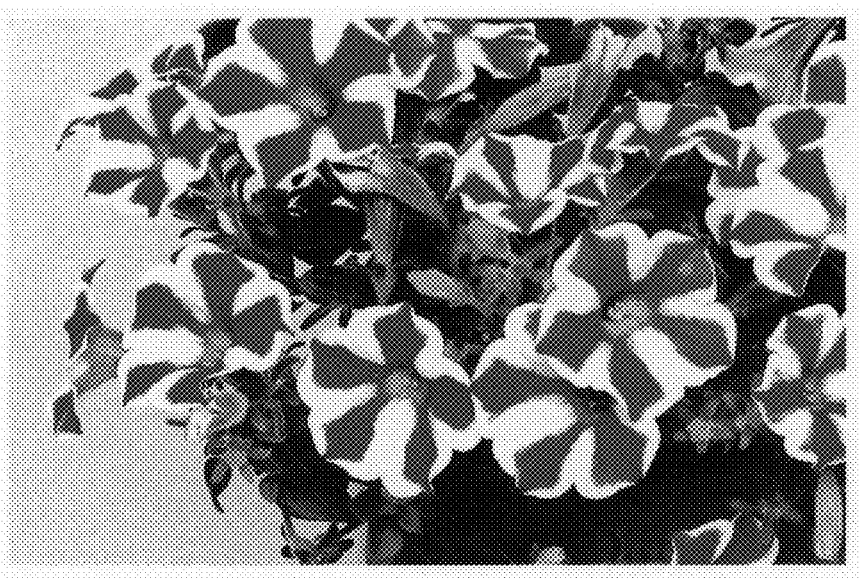
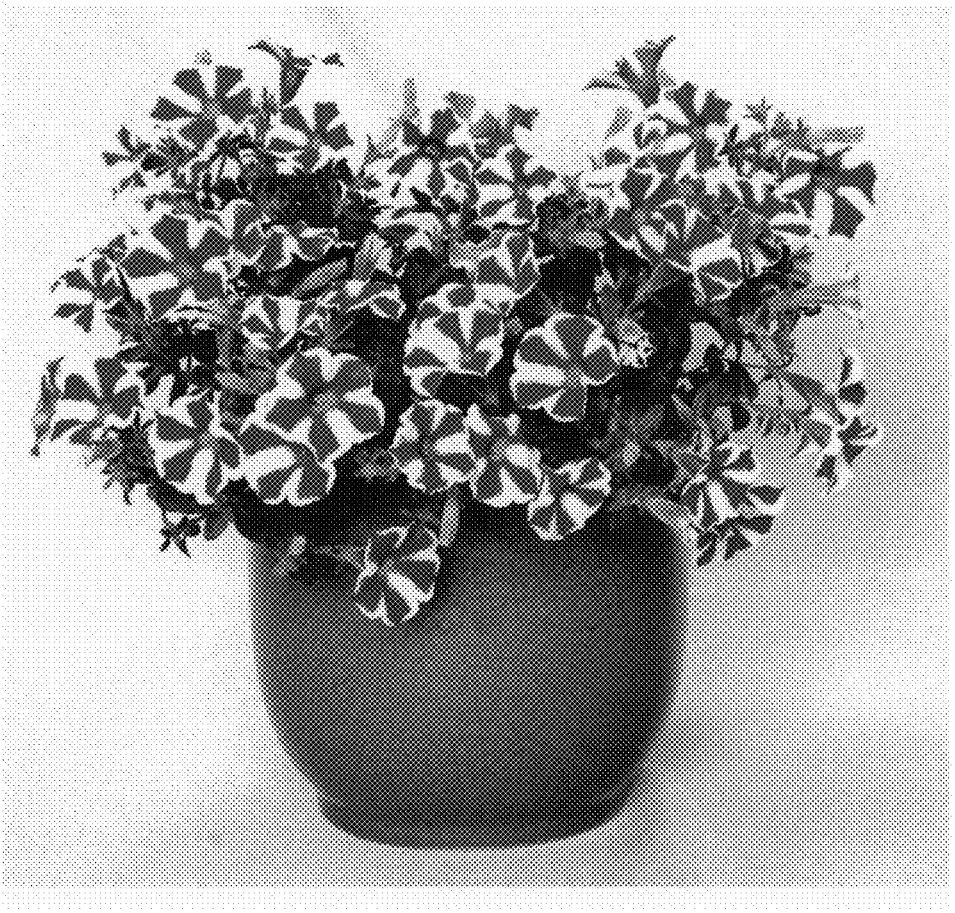

* * * * *